United States Patent [19]

Komatsu et al.

[11] 4,211,882
[45] Jul. 8, 1980

[54] PROCESS FOR PRODUCING TEREPHTHALIC ACID

[75] Inventors: Makoto Komatsu; Tazuo Ohta; Toru Tanaka; Kimiko Akagi, all of Kurashiki, Japan

[73] Assignee: Mitsubishi Gas Chemical Company, Inc., Tokyo, Japan

[21] Appl. No.: 14,597

[22] Filed: Feb. 23, 1979

Related U.S. Application Data

[63] Continuation of Ser. No. 825,480, Aug. 17, 1977, abandoned, which is a continuation of Ser. No. 655,637, Feb. 5, 1976, abandoned.

[30] Foreign Application Priority Data

Feb. 10, 1975 [JP] Japan ................................. 50-17072
Feb. 10, 1975 [JP] Japan ................................. 50-17073

[51] Int. Cl.$^2$ ............................................. C07C 51/33
[52] U.S. Cl. .................................... 562/416; 562/421
[58] Field of Search ............................... 562/421, 416

[56] References Cited

U.S. PATENT DOCUMENTS

| 3,919,305 | 11/1975 | Gay | 562/416 |
| 3,947,494 | 3/1976 | Kuhlmann | 562/416 |

*Primary Examiner*—Alan Siegel
*Attorney, Agent, or Firm*—Armstrong, Nikaido, Marmelstein & Kubovcik

[57] ABSTRACT

Terephthalic acid is produced by oxidizing, in a liquid phase, p-tolualdehyde with a gas containing molecular oxygen, for example, air, in the presence of a catalyst consisting each of (1) a manganese compound, (2) a cobalt compound, (3) a bromine compound, and (4) at least one compound selected from the group consisting of chromium compounds, iron compounds, nickel compounds and compounds of metallic elements belonging to the lanthanide series, using a lower aliphatic monocarboxylic acid as a solvent.

25 Claims, No Drawings

PROCESS FOR PRODUCING TEREPHTHALIC ACID

This application is a continuation application of application Ser. No. 825,480 filed Aug. 17, 1977. Application Ser. No. 825,480, in turn, is a continuation application of application Ser. No. 655,637 filed Feb. 5, 1976. The prior applications are now abandoned.

This invention relates to a process for producing terephthalic acid by oxidizing paratolualdehyde, which will be hereinafter referred to as "p-tolualdehyde", with a gas containing molecular oxygen in the presence of heavy metal compounds and a bromine compound, using a lower aliphatic monocarboxylic acid as a solvent, and more particularly a process for producing terephthalic acid by oxidizing, in a liquid phase, p-tolualdehyde with a gas containing molecular oxygen in the presence of a catalyst consisting each of (1) a manganese compound, (2) a cobalt compound, (3) bromine compound and (4) at least one compound selected from the group consisting of chromium compounds, iron compounds, nickel compounds and compounds of metallic elements belonging to the lanthanide series, using a lower aliphatic monocarboxylic acid as a solvent.

A process for producing an aromatic carboxylic acid from the corresponding aromatic compound having at least one aliphatic substituent by oxidizing, in a liquid phase, the aromatic compound with a gas containing molecular oxygen in the presence of a heavy metal compound containing manganese and a bromine compound, using a lower aliphatic monocarboxylic acid as a solvent is disclosed in Japanese Patent Publication No. 2666/59. Said process is characterized by producing a carboxylic acid from the corresponding aromatic compound having an aliphatic substituent in one reaction step utilizing a hydrogen-withdrawing action of bromine ions. Actually said process is industrially utilized for the production of terephthalic acid from p-xylene, isophthalic acid from m-xylene, etc.

All the dicarboxylic acids derived from xylenes by oxidation are important substances as raw materials for the industry, and have various applications. For example, terephthalic acid synthesized from p-xylene has a great industrial significance as a raw material for polyesters such as polyethylene terephthalate, polybutylene terephthalate, etc. or plasticizers derived from terephthalic acid. On the other hand, p-xylene serving as the raw material of the terephthalic acid can be obtained from a xylene mixture by several operation steps such as super-fractionation, fractional crystallization, etc. and then converted to terephthalic acid by oxidation. There may be several methods to obtain terephthalic acid without separating p-xylene from the xylene mixture. For example, the xylene mixture is oxidized according to the process disclosed in Japanese Patent Publication No. 2666/59, etc., and then from the resulting mixture of terephthalic acid, isophthalic acid, phthalic acid, etc. are fractionated their respective acids by utilizing differences in the solubilities of the respective acids in specific solvents, or by reacting the acids with alcohol, subjecting the resulting esters of the acids to fractional distillation utilizing differences in their boiling points, and then hydrolyzing the ester of terephthalic acid thus obtained. However any of these procedures requires several operation steps to obtain terephthalic acid. This complicates the process for producing terephthalic acid, and is not desirable from the viewpoint of cost, etc. Thus, it has been long expected to use another raw material from which terephthalic acid can be obtained in a more simple process.

As the raw materials from which terephthalic acid is obtained in more simple process, intermediates resulting from the reaction converting p-xylene to terephthalic acid by oxidation, such as p-tolualdehyde, p-toluic acid, and 4-carboxybenzaldehyde, can be taken into consideration at first, but among these raw materials the applicable raw materials must be readily synthetically prepared. Fortunately, p-tolualdehyde can be readily synthesized from toluene and carbon monoxide by means of a Friedel-Craft catalyst such as anhydrous aluminum chloride, etc. Furthermore, the industrial scale technique of producing p-tolualdehyde has been also nearly established, and p-tolualdehyde can be supplied in a large amount. Since p-tolualdehyde is a reaction intermediate in the course from p-xylene to terephthalic acid, it is quite expectable that p-tolualdehyde can be readily converted to terephthalic acid by oxidation. In view of the possibility to supply p-tolualdehyde in an industrial scale as well as the necessity to separate p-xylene from a xylene mixture or to separate terephthalic acid from a mixture of terephthalic acid, isophthalic acid, and phthalic acid, as mentioned above, it has a great commercial effect to establish a technique to produce terephthalic acid by the oxidation of p-tolualdehyde without the complicated separating procedures.

It is well known that compounds of metals such as cobalt, manganese, molybdenum, etc. can serve as catalysts for liquid phase air oxidation. In the case of converting aromatic compounds having at least one aliphatic substituent to the corresponding aromatic carboxylic acids through one-step oxidation process, the aromatic carboxylic acids can be efficiently produced by using a catalyst containing a cobalt compound, manganese compound and a bromine compound, and also a lower aliphatic monocarboxylic acid as a solvent, as disclosed in Japanese Patent Publication No. 2666/59. The foregoing technique is also well applicable to the case of producing terephthalic acid from p-xylene. For the production of terephthalic acid from p-xylene through one step oxidation process the absence of any one of the cobalt compound, manganese compound and bromine compound is not effective, and these three constituents are essential for the desired effect.

The present inventors tried to apply said well known system consisting of the cobalt compound, manganese compound and bromine compound to the synthesis of terephthalic acid by oxidation of p-tolualdehyde in a semi-continuous or continuous process on the basis of said observations that p-tolualdehyde is the reaction intermediate in the production of terephthalic acid from p-xylene, p-tolualdehyde is readily prepared from toluene, and the system consisting of the cobalt compound, manganese compound, bromine compound, and lower aliphatic carboxylic acid is effective for the synthesis of terephthalic acid by the oxidation of p-xylene, and as a result found that, in spite of the fact that p-tolualdehyde is the intermediate in the synthesis of terephthalic acid by the oxidation of p-xylene as the raw material, blackened terephthalic acid was obtained in the semi-continuous or continuous process. Such a phenomenon has not been observed yet in the synthesis of terephthalic acid by the oxidation of p-xylene, and was an unexpected result. It is impossible to obtain a polyester having a high whitenes and clearness, and a commercial value, even if the blackened terephthalic acid obtained according to said reaction method is reacted, as such, with glycols.

Furthermore, the present inventors found that the black colour cannot be removed from the terephthalic acid by well known purification procedures such as acetic acid washing or recrystallization from acetic acid or water, or recrystallization from hot water accompanying hydrogenation disclosed in Japanese Patent Publication No. 16860/66. That is, these facts show that in the semi-continuous or continuous process using p-tolualdehyde as the raw material, it is difficult, by the mere application of prior art, to produce terephthalic acid having qualities equal to those of terephthalic acid obtained from p-xylene.

As a result of extensive studies of obtaining industrially valuable terephthalic acid from p-tolualdehyde on such technical backgrounds, the present inventors have found that terephthalic acid having a high whiteness and little impurities can be obtained in a high yield by oxidizing, in a liquid phase, p-tolualdehyde with a gas containing molecular oxygen in the presence of a catalyst consisting each of (1) a manganese compound, (2) a cobalt compound, (3) a bromine compound, and (4) at least one compound selected from the group consisting of chromium compounds, iron compounds, nickel compounds and compounds of metal elements belonging to the lanthanide series, using a lower aliphatic monocarboxylic acid as a solvent, and have established the present invention.

An object of the present invention is to provide terephthalic acid of high purity as keenly desired in the field of polyester fibers, polyester resins or plasticizers derived from the terephthalic acid, without using xylenes as the raw material, which require separation of isomers at the raw material stage or at the product stage.

As the result of studies on the blackening phenomenon of product terephthalic acid, the serious problem in the production of terephthalic acid from p-tolualdehyde as the raw material, the present inventors have found that the blackening phenomenon is due to the manganese compound contained in the product terephthalic acid, and also that the degree of contamination of terephthalic acid with the manganese compound greatly depends upon the water concentration or manganese concentration of reaction medium. That is, the blackening can be suppressed by maintaining the water concentration and manganese concentration in the reaction medium within the concentration ranges as not to bring about the blackening. However, according to the present invention, it is possible to obtain terephthalic acid having a high whiteness and little impurities by simple operation of adding at least one compound selected from chromium compounds, iron compounds, nickel compounds and compounds of metal elements belonging to the lanthanide series as a forth catalyst component to the reaction medium, completely independently of the water concentration and manganese concentration.

According to the present invention, more advantages can be obtained as follows:

Since no blackening phenomenon appears when at least one of these compounds is added to the reaction medium as the fourth component, it is possible to increase the manganese concentration, thereby enhancing a terephthalic acid yield. At the same time, an oxidation loss of the lower aliphatic monocarboxylic acid used as the solvent can be suppressed, and a recovery ratio of the lower aliphatic monocarboxylic acid is increased. The recovery ratio of the lower aliphatic monocarboxylic acid depends upon species of metal elements as the fourth component of the catalyst to be added, and chromium compounds, lanthanum compounds and cerium compounds show the best results. In view of the fact that iron compounds, nickel compounds and compounds of metal elements belonging to the lanthanide series other than lanthanum and cerium show second-best results, the chromium compounds, lanthanum compounds and cerium compounds are the most preferable as the fourth component of catalyst.

In the present invention, it is desirable to use the cobalt compounds, manganese compounds, chromium compounds, iron compounds, nickel compounds and compounds of metal elements belonging to the lanthanide series, which are all soluble in a lower aliphatic monocarboxylic acid as the solvent. They can be used in any form of inorganic acid salts and organic acid salts, and, in the case of the metal elements belonging to the lanthanide series, their hydroxides can be also used. The respective metal elements of cobalt, manganese, chromium, iron, and the lanthanide series can take a plurality of stable valences, but in the present invention, the metal elements of any valency can be used.

The manganese compounds effective for the present invention include inorganic acid salts such as manganese bromide, manganese carbonate, etc., or organic acid salts such as manganese formate, manganese acetate, manganese propionate, manganese butyrate, manganese valerate, manganese naphthenate, etc., and it is preferable to add 0.001 to 2.5% by weight of the manganese compound, in terms of manganese atoms of the manganese compound added, to the reaction medium, on the basis of the solvent.

The cobalt compounds effective for the present invention include inorganic acid salts such as cobalt bromide, cobalt carbonate, etc., and organic acid salts such as cobalt formate, cobalt acetate, cobalt propionate, cobalt butyrate, cobalt valerate, cobalt naphthenate etc., and it is preferable to add 0.005 to 0.5% by weight of the cobalt compound, in terms of cobalt atoms of the cobalt compound added, to the reaction medium, on the basis of the solvent.

The bromine compounds effective for the present invention include inorganic acids such as hydrobromic acid, inorganic acid salts such as ammonium bromide, sodium bromide, potassium bromide, cesium bromide, magnesium bromide, barium bromide, etc., or organobromic compounds such as tetraalkylammonium bromide, tetrabromoethane, tetrabromoparaxylene, etc., and it is preferable to add 0.05 to 0.5% by weight of the bromine compound, in terms of bromine atoms of the bromine compound added, to the reaction medium, on the basis of the solvent.

The chromium compounds effective for the present invention include inorganic acid salts such as chromium bromide, chromium carbonate, etc., or chromium oxides, or chromates such as sodium chromate, potassium chromate, etc., or organic acid salts such as chromium formate, chromium acetate, chromium propionate, chromium butyrate, chromium valerate, etc., and it is preferable to add the chromium compound to the reaction medium at an atomic ratio of the chromium atoms of the chromium compound added to the manganese atoms of the manganese compounds added, that is, Cr/Mn, of 0.7 to 30.0.

The iron compounds effective for the present invention include inorganic acid salts such as iron bromide, iron carbonate, etc., or organic acid salts such as iron formate, iron acetate, iron propionate, iron butyrate, iron valerate, iron oxalate, etc., and it is desirable to add the iron compound to the reaction medium at a ratio of the iron atoms of the iron compound added to the manganese atoms of the manganese compound added, that is, Fe/Mn, of 0.7 to 30.0.

The nickel compounds effective for the present invention include inorganic acid salts such as nickel bromide, nickel carbonate, etc., or organic acid salts such as nickel formate, nickel acetate, nickel propionate, nickel butyrate, nickel valerate, etc., and it is desirable to add the nickel compound to the reaction medium at a ratio of the nickel atoms of the nickel compound added to the manganese atoms of the manganese compound added, that is, Ni/Mn, of 0.7 to 30.0.

The metal elements belonging to the lantanide series effective for the present invention are lanthanum, cerium, praseodymium, neodymium, samarium, europium, gadolinium, terbium, dysprosium, holmium, erbium, thulium, ytterbium, and lutetium.

The lanthanum compounds include inorganic acid salts such as lanthanum chloride, lanthanum bromide, lanthanum carbonate, etc., or organic acid salts such as lanthanum formate, lanthanum acetate, lanthanum propionate, lanthanum butyrate, lanthanum valerate, etc., or lanthanum hydroxide.

The cerium compounds include inorganic acid salts such as cerium chloride, cerium bromide, cerium carbonate, etc., or organic acid salts such as cerium formate, cerium acetate, cerium propionate, cerium butyrate, cerium valerate, etc., or cerium hydroxide.

The praseodymium compounds include inorganic acid salts such as praseodymium chloride, praseodymium bromide, praseodymium carbonate, etc., or organic acid salts such as praseodymium formate, praseodymium acetate, praseodymium propionate, praseodymium butyrate, praseodymium valerate, etc., or praseodymium hydroxide.

The neodymium compounds include inorganic acid salts such as neodymium chloride, neodymium bromide, neodymium carbonate, etc., or organic acid salts such as neodymium formate, neodymium acetate, neodymium propionate, neodymium butyrate, neodymium valerate, etc., or neodymium hydroxide.

The samarium compounds include inorganic acid salts such as samarium chloride, samarium bromide, samarium carbonate, etc., or organic acid salts such as samarium formate, samarium acetate, samarium propionate, samarium butyrate, samarium valerate, etc. or samarium hydroxide.

The eruopium compounds include inorganic acid salts such as europium chloride, europium bromide, europium carbonate, etc., or organic acid salts such as europium formate, europium acetate, europium propionate, europium butyrate, europium valerate, etc., or europium hydroxide.

The gadolinium compounds include inorganic acid salts such as gadolinium chloride, gadolinium bromide, gadolinium carbonate, etc., or organic acid salts such as gadolinium formate, gadolinium acetate, gadolinium propionate, cadolinium butyrate, gadolinium valerate, etc. or gadolinium hydroxide.

The terbium compounds include inorganic acid salts such as terbium chloride, terbium bromide, terbium carbonate, etc., or organic acid salts such as terbium formate, terbium acetate, terbium propionate, terbium butyrate, terbium valerate, etc., or terbium hydroxide.

The dysprosium compounds include inorganic acid salts such as dysprosium chloride, disprosium bromide, dysprosium carbonate, etc., or organic acid salts such as dysprosium formate, dysprosium acetate, dysprosium propionate, dysprosium butyrate, dysprosium valerate, etc., or dysprosium hydroxide.

The holmium compounds include inorganic acid salts such as holmium chloride, holmium bromide, holmium carbonate, etc., or organic acid salts such as holmium formate, holmium acetate, holmium propionate, holmium butyrate, holmium valerate, etc., or holmium hydroxide.

The erbium compounds include inorganic acid salts such as erbium chloride, erbium bromide, erbium carbonate, etc., or organic acid salts such as erbium formate, erbium acetate, erbium propionate, erbium butyrate, erbium valerate, etc., or erbium hydroxide.

The thulium compounds include inorganic acid salts such as thulium chloride, thulium bromide, thulium carbonate, etc., or organic acid salts such as thulium formate, thulium acetate, thulium propionate, thulium acetate, thulium valerate, etc., or thulium hydroxide.

The ytterbium compounds include inorganic acid salts such as ytterbium chloride, ytterbium bromide, ytterbium carbonate, etc., or organic acid salts such as ytterbium formate, ytterbium acetate, ytterbium propionate, ytterbium butyrate, ytterbium valerate, etc., or ytterbium hydroxide.

The lutetium compounds include inorganic acid salts such as lutetium chloride, lutetium bromide, lutetium carbonate, etc., or organic acid salts such as lutetium formate, lutetium acetate, lutetium propionate, lutetium butyrate, lutetium valerate, etc., or lutetium hydroxide.

It is desirable to add the lanthanide compound to the reaction medium at an atomic ratio of the metallic atoms belonging to the lanthanide series in the lanthanide compound added to the manganese atoms of the manganese compound added, that is, lanthanide to Mn, of 0.02 to 10.0.

As the lower aliphatic monocarboxylic acid as the solvent, acetic acid, propionic acid, butyric acid, etc. can be used, but acetic acid is particularly preferable. It is preferable to use the solvent in an amount of at least twice by weight as much as the weight of p-tolualdehyde.

Reaction temperature suitable for the practice of the present invention is in a range of 120° to 260° C., preferably 160° to 250° C. The reaction is carried out in a liquid phase, so it is necessary to apply a pressure to the reaction system to maintain p-tolualdehyde and the solvent in a liquid phase. The degree of pressure is such as to maintain the reaction system (raw materials and solvent) in a liquid phase in said reaction temperature range. Usually, the pressure is in a range of 0.5 to 50 kg/cm$^2$ gauge.

As an oxidizing agent, oxygen or a gas containing the molecular oxygen, such as air, can be used, but the use of air is economically advantageous.

In the present invention, the reaction can be carried out in a semi-continuous or continuous process. It is enough to use the reaction conditions such as feed rate of p-tolualdehyde, feed rate of air, and, in the case of the continuous process, residence time of the reaction solution in a reactor, etc., which belong to the prior art in the synthesis of terephthalic acid from p-xylene.

Effects of the present invention will be described below, in comparison with the case of oxidation of p-tolualdehyde using the well known catalyst system consisting of a cobalt compound, manganese compound and bromine compound.

After charging acetic acid and a catalyst into a reactor vessel, p-tolualdehyde is continuously fed to the reactor vessel at an elevated temperature under superatmosphere at a constant rate over a definite period of time, while feeding air thereto. The resulting product is filtered, washed with acetic acid and water, and terephthalic acid is obtained thereby. Reaction conditions, properties and yield of terephthalic acid thus obtained, and recovery ratio of acetic acid are shown in Table 1.

thermore, the recovery ratio of acetic acid and the terephthalic acid yield are lower.

Even if the dark grey terephthalic acid obtained by using the prior art catalyst system is subjected to hydrogenation in the presence of a catalyst, and then to recrystallization from hot water according to the procedure disclosed in Japanese Patent Publication No. 16860/66, the alkaline color is not improved. The polyethylene terephthalate resulting from the reaction of this dark grey terephthalic acid with ethyleneglycol is also greyish and unclear. On the other hand, when the terephthalic acid obtained by the oxidation of p-tolualdehyde in the presence of the catalysts containing a compound selected from the group consisting of the chromium compounds, iron compounds, nickel com- Table 1

| | | Prior art | Present invention | | | | | |
|---|---|---|---|---|---|---|---|---|
| | | | Cr compound | Fe compound | Ni compound | La compound | Ce compound | Eu compound |
| | p-Tolualdehyde (duration for addition) | 80 g (1 hr) | 80 g (1 hr) | 80 g (1 hr) | 80 g (1 hr) | 80 g (1 hr) | 80 g (1 hr) | 80 g (1 hr) |
| | Reaction temperature, °C. | 205 | 205 | 205 | 205 | 205 | 205 | 205 |
| | Reaction pressure, kg/cm$^2$ gauge | 20 | 20 | 20 | 20 | 20 | 20 | 20 |
| | Acetic acid (95% purity), g | 210 | 210 | 210 | 210 | 210 | 210 | 210 |
| Reaction Conditions | Cobalt acetate, g | 0.5330 (0.060)$^d$ | 0.5330 (0.060)$^d$ | 0.5330 (0.060)$^d$ | 0.5330 (0.060)$^d$ | 0.5330 (0.060)$^d$ | 0.5330 (0.060)$^d$ | 0.5330 (0.060)$^d$ |
| | Manganese acetate, g | 0.0937 (0.010) | 0.0937 (0.010) | 0.0937 (0.010) | 0.0937 (0.010) | 0.0468 (0.005) | 0.0468 (0.005) | 0.0468 (0.005) |
| | Sodium bromide, g | 0.3240 (0.120) | 0.3240 (0.120) | 0.3240 (0.120) | 0.3240 (0.120) | 0.3240 (0.120) | 0.3240 (0.120) | 0.3240 (0.120) |
| | Fourth component, g | None | Chromic acetate 0.1890 (0.0189) | Ferrous oxalate 0.1375 (0.0203) | Nickel acetate 0.1904 (0.0214) | Lanthanum acetate 0.0560 (0.0104) | Cerium acetate 0.0641 (0.0128) | Europium chloride 0.0700 (0.0138) |
| | Atomic ratio of fourth component to Manganese | | 2.0 | 2.0 | 2.0 | 0.8 | 1.0 | 1.0 |
| Properties of terephthalic acid | Appearance | Dark grey | White | White | White | White | White | White |
| | Alkaline color$^a$ | ∞ | 0.514 | 0.664 | 0.610 | 0.473 | 0.423 | 0.572 |
| | 4 CBA content$^b$, ppm | 830 | 723 | 753 | 740 | 610 | 587 | 680 |
| | Ashes, ppm | 93 | 3.7 | 4.1 | 4.0 | 3.0 | 2.5 | 4.2 |
| Terephthalic acid yield, % | | 95.1 | 97.3 | 96.3 | 96.8 | 96.8 | 97.1 | 96.5 |
| Acetic acid recovery ratio$^c$, % | | 84.1 | 93.0 | 90.5 | 90.2 | 91.0 | 91.5 | 89.7 |

Notes:
$^a$2 g of sample is dissolved in 25 ml of an aqueous 2N potassium hydroxide solution, and then the solution is placed in a 50 mm cell to measure absorption spectrum. Absorbancy at 340 mμ.
$^b$4-carboxybenzaldehyde is abbreviated as 4 CBA. Its content in the resulting terephthalic acid, ppm.
$^c$After filtration of the product, an acetic acid content of the resulting filtrate is quantitatively determined by gas chromatography. A ratio of the residual acetic acid to the charged acetic acid is given.
$^d$Figure in parentheses means a percentage by weight of metal atoms or bromine atoms in the metal compounds compoundsk or bromine compound used as the catalyst to acetic acid, respectively.

It is seen from Table 1, especially, the appearance and measurement of alkaline color, that when a compound selected from the chromium compound, iron compound, nickel compound, lanthanum compound, cerium compound and europium compound is added to the prior art catalyst as the fourth component of the catalyst, blackening can be prevented and terephthalic acid having a high whiteness can be obtained, as compared with the well known catalyst system consisting only of the cobalt compound, manganese compound, and bromine compound. Furthermore, it is seen from the low ash content that contamination of terephthalic acid with the catalyst components is less, and furthermore the terephthalic acid yield is higher. Furthermore, since the acetic acid loss is suppressed, the recovery ratio of acetic acid is increased.

In the case that no fourth component is added to the catalyst system, the resulting terephthalic acid contains a more amount of ashes, that is, inorganic components, and, in other words, the product terephthalic acid is much contaminated with the catalyst components. Furpounds and lanthanide compounds is treated in the same process as above, its purity can be further enhanced. Furthermore, the polyethylene terephthalate resulting from said terephthalic acid with ethyleneglycol is colorless and clear. That is, not only in terephthalic acid itself, but also in polyehtylene terephthalate, there are considerable differences between the present invention and the prior art. Anyway, it is apparent that the presence of the compound selected from the group consisting of the chromium compounds, iron compounds, nickel compounds, and lanthanide compounds gives an advantageous influence upon the oxidation reaction, enabling the production of terephthalic acid of high whiteness and high purity. The chromium compounds, lanthanum compounds or cerium compounds generally give a better result than the iron compound, nickel compound or compounds of the lanthanide series other than the lanthanum compound and cerium compound, and especially gives an excellent result in the recovery ratio of the lower aliphatic monocarboxylic acid. Thus, the chromium compounds, lanthanum compounds, and cerium compounds are preferable substances among the chromium compounds, iron compounds, nickel compounds, and lanthanide compounds.

The present invention will be described in detail below, referring to Examples.

EXAMPLES 1 AND 2

Into a titanium pressure-resistant reactor vessel (capacity: 500 ml) provided with a reflux condenser, stirrer, and heater, and also a feed inlet and feed gas inlet, were charged in advance 210 g of 95% acetic acid as a solvent, and also cobalt acetate tetrahydrate, manganous acetate tetrahydrate, sodium bromide and chromic acetate monohydrate as a catalyst in the respective amounts (in weight) shown in Table 2.

As shown in Table 2, the pressure of the reactor vessel charged with the catalyst and the solvent was increased to 10 kg/cm$^2$ gauge with a nitrogen gas, and then the temperature of the reactor vessel was elevated to 205° C. by means of the heater. Then, 80 g (0.666 moles) of p-tolualdehyde as a raw material was continuously fed to the reactor vessel at a constant rate over a period of one hour, while placing the content of the reactor vessel to vigorous stirring at a temperature of 205° C. and a pressure of 20 kg/cm$^2$ gauge and feeding air to the reactor vessel. The air was further fed thereto for 5 minutes after the end of the raw material feeding, and then the reactor vessel was cooled, and the resulting reaction solution having slurry was withdrawn from the reactor vessel.

The withdrawn reaction solution was filtered through a glass filter, and the resulting cake was washed with acetic acid, and then with water, and dried at 110° C. In Example 1, 107.0 g of terephthalic acid was obtained, and in Example 2, 180.0 g of terephthalic acid was obtained. The properties and yield of the resulting terephthalic acid, and recovery ratio of acetic acid are shown in Table 2. In Table 2, the alkaline color, 4 CBA content, and recovery ratio of acetic acid were measured in the same way as in Table 1 and have the same significances as in Table 1.

When terephthalic acid obtained in Examples 1 and 2 were subjected to hydrogenation with molecular hydrogen in the presence of a catalyst and recrystallization according to the procedure disclosed in Japanese Patent Publication No. 16860/66, the resulting purified terephthalic acid has an appearance of whiteness, and alkaline color of less than 0.090, and 4CBA content of less than 10 ppm. Furthermore, polyethylene terephthalate obtained by reaction of said purified terephthalic acid with ethylene glycol was colorless and clear.

EXAMPLES 3 AND 4

Into the same reactor vessel used in Example 1 were charged in advance 210 g of 95% acetic acid, and cobalt acetate tetrahydrate, manganous acetate tetrahydrate, sodium bromide, and chromium (VI) oxide in the respective amounts (in weight) as shown in Table 2. 80 g (0.666 moles) of p-tolualdehyde was continuously fed to the reactor vessel at a constant rate over a period of one hour and subjected to oxidation in the same way as in Example 1, while feeding air to the reactor vessel at a temperature of 205° C. and a pressure of 20 kg/cm$^2$ gauge. The resulting product was treated in the same way as in Example 1, and 106.8 g and 107.7 g of terephthalic acid were obtained in Example 3 and Example 4, respectively. The properties and yield of the resulting terephthalic acid, and recovery ratio of acetic acid are shown in Table 2.

EXAMPLE 5

Into the same reactor vessel as used in Example 1 were charged in advance 210 g of 95% acetic acid, and colbalt acetate tetrahydrate, manganous acetate tetrahydrate, tetrabromoethane, and potassium chromate in the respective amounts (in weight) as given in Table 2.

80 g (0.666 moles) of p-tolualdehyde was continuously fed into the reactor vessel charged with the catalyst and the solvent at a constant rate over a period of 40 minutes and subjected to oxidation in the same way as in Example 1, while feeding air to the reactor vessel at a temperature of 225° C. and a pressure of 25 kg/cm$^2$ gauge. The resulting product was treated in the same way as in Example 1, and 107.1 g of terephthalic acid was obtained. The properties and yield of the resulting terephthalic acid, and recovery ratio of acetic acid are shown in Table 2.

EXAMPLE 6

Into the same reactor vessel as used in Example 1 were charged in advance 210 g of 95% acetic acid, and cobalt acetate tetrahydrate, manganous acetate tetrahydrate, sodium bromide and chromic acetate monohydrate in the respective amounts (in weight) as given in Table 2.

60 g (0.499 moles) of p-tolualdehyde was continuously fed into the reactor vessel charged with the catalyst and the solvent acetic acid as solvent at a constant rate over a period of 2 hours and subjected to oxidation in the same way as in Example 1, while feeding air to the reactor vessel at a temperature of 200° C. and a pressure of 20 kg/cm$^2$ gauge. The resulting product was treated in the same way as in Example 1, and 80.1 g of terephthalic acid was obtained. The properties and yield of the resulting terephthalic acid, and recovery ratio of acetic acid are shown in Table 2.

EXAMPLE 7

Oxidation of p-tolualdehyde was carried out in a continuous reaction apparatus consisting of a titanium pressure-resistant reactor vessel (capacity: 2.5 l) provided with a reflux condenser, stirrer, and heater, and also a feed inlet, feed gas inlet, gas outlet, and product outlet, and two product receivers connected in series to the product outlet.

That is, 500 g of 95% acetic acid, and cobalt acetate tetrahydrate, manganous acetate tetrahydrate, sodium bromide, and chromic acetate monohydrate in the respective amounts (in weight) as shown in Table 2 were charged into the reactor vessel, and the pressure of the reactor vessel was increased to 10 kg/cm$^2$ gauge with nitrogen. Then, the temperature of the reactor vessel was elevated to 220° C. After the elevation of temperature, a feed solution of p-tolualdehyde and the catalyst dissolved in acetic acid was continuously fed to the reactor vessel at a rate of 1,500 g of the solution (375 g of p-tolualdehyde) per hour, while feeding air to the reactor vessel at a reaction temperature of 220° C. and a pressure of 24 kg/cm$^2$ gauge. The resulting reaction product slurry was continuously withdrawn from the reactor vessel, while keeping the liquid level constant in the reactor vessel. Ratio by weight of acetic acid to p-tolualdehyde in the feed solution was 3.0.

The withdrawn reaction product slurry was filtered, and the resulting cake was washed twice each with acetic acid and water, and then dried at 110° C., whereby 501.0 g of terephthalic acid was obtained per four. Properties and yield of terephthalic acid thus obtained, and recovery ratio of acetic acid are shown in Table 2.

The resulting terephthalic acid was then subjected to hydrogenation with molecular hydrogen in the presence of a catalyst and recrystallization from hot water according to the procedure disclosed in Japanese Patent Publication No. 16860/66. The resulting purified terephthalic acid has an appearance of whiteness, alkaline color of 0.040, and 4CBA content of 2 ppm.

Polyethylene terephthalate obtained by reaction of the purified terephthalic acid with ethyleneglycol was colorless and clear.

EXAMPLE 8

Into the same reactor as used in Example 1 were charged 210 g of 95% acetic acid, and cobalt acetate tetrahydrate, manganous acetate tetrahydrate, sodium bromide, and ferrous oxalate dihydrate in the respective amounts (in weight) as shown in Table 3.

80 g (0.666 moles) of p-tolualdehyde was continuously fed into the reactor vessel at a constant rate over a period of one hour and subjected to oxidation in the same way as in Example 1, while feeding air to the reactor vessel at a temperature of 205° C. and a pressure of 20 kg/cm$^2$ gauge. The resulting product was treated in the same way as in Example 1, whereby 107.2 g of terephthalic acid was obtained.

Properties and yield of the terephthalic acid thus obtained, and recovery ratio of acetic acid are given in Table 3.

EXAMPLE 9

Into the same reactor vessel as used in Example 1 were charged 210 g of 95% acetic acid, and cobalt acetate tetrahydrate, manganous acetate tetrahydrate, sodium bromide and nickel acetate in the respective amounts (in weight) as shown in Table 3.

80 g (0.666 moles) of p-tolualdehyde was continuously fed to the reactor vessel at a constant rate over a period of one hour and subjected to oxidation in the same way as in Example 1, while feeding air to the reactor vessel at a temperature of 205° C. and a pressure of 20 kg/cm$^2$ gauge. The resulting product was treated in the same way as in Example 1, whereby 107.3 g of terephthalic acid was obtained.

Properties and yield of the terephthalic acid thus obtained, and recovery ratio of acetic acid are shown in Table 3.

EXAMPLE 10

Into the same reactor vessel as used in Example 1 were charged 210 g of 95% acetic acid, and cobalt acetate tetrahydrate, manganous acetate tetrahydrate, sodium bromide and nickel acetate in the respective amounts (in weight), as shown in Table 3.

40 g (0.333 moles) of p-tolualdehyde was continuously fed at a constant rate over a period of one hour, and subjected to oxidation in the same way as in Example 1, while feeding air to the reactor vessel at a temperature of 200° C. and a pressure of 20 kg/cm$^2$ gauge. The resulting product was treated in the same way as in Example 1, whereby 53.4 g of terephthalic acid was obtained.

Properties and yield of the terephthalic acid thus obtained, and recovery ratio of acetic acid are shown in Table 3.

EXAMPLE 11

Into the same reactor vessel as used in Example 1 were charged 210 g of 95% acetic acid, and cobalt acetate tetrahydrate, manganous acetate tetrahydrate, sodium bromide, and lanthanum acetate dihydrate in the respective amounts (in weight) as shown in Table 4.

The pressure of the reactor vessel charged with the catalyst and the solvent acetic acid was increased to 10 kg/cm$^2$ gauge with a nitrogen gas, and then the temperature of the reactor vessel was elevated to 195° C. by mans of the heater. Then, 80 g (0.666 moles) of p-tolualdehyde was continuously fed to the reactor vessel at a constant rate over a period of one hour together with air, while stirring the content of the reactor vessel at a temperature of 195° C. and a pressure of 17 kg/cm$^2$ gauge. Air was further fed thereto for five minutes after the end of feeding the raw material p-tolualdehyde, and then the reactor vessel was cooled, and the resulting product slurry was withdrawn from the reactor vessel.

The withdrawn product slurry was filtered through a glass filter, and the resulting cake was washed with acetic acid, and then with water, and dried at 110° C., whereby 107.5 g of terephthalic acid was obtained.

Properties and yield of the terephthalic acid thus obtained, and recovery ratio of acetic acid are shown in Table 4.

EXAMPLE 12

Into the same reactor vessel as in Example 1 were charged 210 g of 95% acetic acid, and cobalt acetate tetrahydrate, manganous acetate tetrahydrate, sodium bromide and lanthanum acetate dihydrate in the respective amounts (in weight) as shown in Table 4.

80 g (0.666 moles) of p-tolualdehyde was continuously added to the reactor vessel charged with the catalyst and acetic acid at a constant rate over a period of one hour, and subjected to oxidation in the same way as in Example 11, while feeding air to the reactor vessel at a temperature of 210° C. and a pressure of 20 kg/cm$^2$ gauge. The resulting product was treated in the same way as in Example 11, whereby 107.2 g of terephthalic acid was obtained.

Properties and yield of the terephthalic acid thus obtained, and recovery ratio of acetic acid are shown in Table 4.

EXAMPLE 13

Into the same reactor vessel as in Example 1 were charged 210 g of 95% acetic acid, and cobalt acetate tetrahydrate, manganous acetate tetrahydrate, sodium bromide, and cerium acetate monohydrate in the respective amounts (in weight) as shown in Table 4.

80 g (0.666 moles) of p-tolualdehyde was continuously fed to the reactor vessel charged with the catalyst and the solvent at a constant rate over a period of one hour, and subjected to oxidation in the same way as in Example 11, while feeding air to the reactor vessel at a temperature of 195° C. and a pressure of 17 kg/cm$^2$ gauge. The resulting product was treated in the same way as in Example 11, whereby 107.8 g of terephthalic acid was obtained.

Properties and yield of the terephthalic acid thus obtained, and recovery ratio of acetic acid are shown in Table 4.

EXAMPLE 14

Into the same reactor vessel as used in Example 1 were charged 210 g of 95% acetic acid, and cobalt acetate tetrahydrate, manganous acetate tetrahydrate, sodium bromide and cerium acetate monohydrate in the respective amounts (in weight) as shown in Table 4.

60 g (0.499 moles) of p-tolualdehyde was continuously fed to the reactor vessel charged with the catalyst and the solvent acetic acid at a constant rate over a period of two hours and subjected to oxidation in the same way as in Example 11, while feeding air to the reactor vessel at a temperature of 200° C. and a pressure of 20 kg/cm$^2$ gauge. The resulting product was treated in the same way as in Example 11, whereby 79.7 g of terephthalic acid was obtained.

Properties and yield of the terephthalic acid thus obtained, and recovery ratio of acetic acid are shown in Table 4.

EXAMPLE 15

Into the same reactor vessel as used in Example 1 were charged 210 g of 95% acetic acid, and cobalt acetate tetrahydrate, manganous acetate tetrahydrate, sodium bromide and cerium acetate monohydrate in the respective amounts (in weight) as shown in Table 4.

80 g (0.666 moles) of p-tolualdehyde was continuously fed to the reactor vessel charged with the catalyst and the solvent acetic acid at a constant rate over a period of one hour and subjected to oxidation in the same way as in Example 11, while feeding air to the reactor vessel at a temperature of 210° C. and a pressure of 20 kg/cm$^2$ gauge. The resulting product was treated in the same way as in Example 11, whereby 107.8 g of terephthalic acid was obtained.

Properties and yield of the terephthalic acid thus obtained, and recovery ratio of acetic acid are shown in Table 4.

EXAMPLES 16-18

Into the same reactor vessel as used in Example 1 were charged 210 g of 95% acetic acid, and cobalt acetate tetrahydrate, manganous acetate tetrahydrate, sodium bromide, and neodymium carbonate octahydrate in the case of Example 16, gadolinium chloride hexahydrate in the case of Example 17, or holmium chloride hexahydrate in the case of Example 18 in the respective amounts (in weight) as shown in Table 4.

80 g (0.666 moles) of p-tolualdehyde was continuously fed to the reactor vessel charged with the catalyst and the solvent acetic acid at a constant rate over a period of one hour, and subjected to oxidation in the same way as in Example 11, while feeding air to the reactor vessel at a temperature of 205° C. and a pressure of 10 kg/cm$^2$ gauge. The resulting product was treated in the same way as in Example 11, whereby 107.5 g of terephthalic acid was obtained in Example 16, 106.3 g of terephthalic acid in Example 17, and 106.3 g of terephthalic acid in Example 18.

Properties and yield of the terephthalic acid, and recovery ratio of acetic acid are shown in Table 4.

When the resulting terephthalic acid was subjected to purification comprising hydrogenation with molecular hydrogen in the presence of a catalyst and recrystallization from hot water as disclosed in Japanese Patent Publication No. 16860/66, all the resulting purified terephthalic acid had an appearance of whiteness, an alkaline color of less than 0.090, and 4CBA content of less than 10 ppm. Polyethylene terephthalate obtained by reaction of the resulting purified terephthalic acid with ehtyleneglycol was colorless and clear.

Table 2

|  |  | Example 1 | Example 2 | Example 3 | Example 4 | Example 5 | Example 6 | Example 7 |
|---|---|---|---|---|---|---|---|---|
| Catalyst | Cobalt compound (g) | Cobalt acetate 0.5330 (0.060) | Cobalt acetate 0.5330 (0.060) | Cobalt acetate 0.1330 (0.015) | Cobalt acetate 1.7800 (0.200) | Cobalt acetate 0.2660 (0.030) | Cobalt acetate 1.7800 (0.200) | Cobalt acetate 1.2700 (0.060) |
|  | Manganese compound (g) | Manganese acetate 0.0468 (0.005) | Manganese acetate (0.1870) (0.020) | Manganese acetate 0.0468 (0.005) | Manganese acetate 0.2810 (0.030) | Manganese acetate 0.8430 (0.090) | Manganese acetate 0.0937 (0.010) | Manganese acetate 0.1340 (0.006) |
|  | Bromine compound (g) | Sodium bromide 0.3240 (0.120) | Sodium bromide 0.3240 (0.120) | Sodium bromide 0.3240 (0.120) | Sodium bromide 0.8110 (0.300) | Tetrabromoethane 0.4540 (0.200) | Sodium bromide 0.6760 (0.250) | Sodium bromide 0.7730 (0.120) |
|  | Fourth component (g) | Chromium acetate 0.0472 (0.00472) | Chromium acetate 0.3780 (0.0378) | Chromium (VI) oxide 0.3630 (0.090) | Chromium (VI) oxide 0.8080 (0.200) | Potassium chromate 1.4100 (0.180) | Chromium acetate (0.100) (0.100) | Chromium acetate (0.060) (0.060) |
|  | Atomic ratio of fourth component to manganese | 1.0 | 2.0 | 19.0 | 7.0 | 2.1 | 10.6 | 10.6 |
| Properties of terephthalic acid | Appearance | White | White | White | White | White | White | White |
|  | Alkaline color | 0.574 | 0.529 | 0.865 | 0.379 | 0.473 | 0.130 | 0.750 |
|  | 4CBA content (p.p.m.) | 730 | 705 | 965 | 465 | 432 | 200 | 1200 |
|  | Ashes (p.p.m.) | 3.5 | 3.8 | 3.1 | 5.3 | 3.7 | less than 3.7 | 2.1 |
| Terephthalic acid yield (%) |  | 96.7 | 97.6 | 96.9 | 97.3 | 96.8 | 96.5 | 96.5 |
| Acetic acid recovery ratio (%) |  | 91.7 | 94.5 | 92.2 | 93.1 | 92.5 | 93.4 | 95.3 |

Note:
Figure in parentheses means a percentage by weight of metal atoms or bromine atoms in the metal compounds or bromine compound used as the catalyst to acetic acid, respectively.

Table 3

|  | Example 8 | Example 9 | Example 10 |
|---|---|---|---|
| Catalyst compound | Cobalt acetate | Cobalt acetate | Cobalt acetate |

Table 3-continued

|  |  | Example 8 | Example 9 | Example 10 |
|---|---|---|---|---|
| Catalyst | (g)<br>Manganese compound<br>(g)<br>Bromine compound<br>(g)<br>Fourth component<br>(g)<br>Atomic ratio of<br>fourth component<br>to manganese | 0.7990 (0.090)<br>Manganese acetate<br>0.1870 (0.020)<br>Sodium bromide<br>0.5410 (0.200)<br>Ferric oxalate<br>0.5500 (0.081)<br><br>4.0 | 0.7990 (0.090)<br>Manganese acetate<br>0.1870 (0.020)<br>Sodium bromide<br>0.5410 (0.200)<br>Nickel acetate<br>0.7610 (0.086)<br><br>4.0 | 1.7800 (0.200)<br>Manganese acetate<br>0.1870 (0.020)<br>Sodium bromide<br>0.6760 (0.250)<br>Nickel acetate<br>0.8900 (0.100)<br><br>4.7 |
| Properties of<br>terephthallic acid | Appearance<br>Alkaline color<br>4CBA content (p.p.m.)<br>Ashes (p.p.m.) | White<br>0.603<br>717<br>3.7 | White<br>0.580<br>710<br>3.8 | White<br>0.250<br>280<br>2.7 |
| Terephthalic acid yield (%) | | 96.9 | 97.0 | 96.5 |
| Acetic acid recovery<br>ratio (%) | | 90.7 | 90.5 | 90.4 |

Note:
Figure in parentheses means a percentage by weight of metal atoms or bromine atoms in the metal compounds or bromine compound used as the catalyst to acetic acid, respectively.

Table 4

|  |  | Example 11 | Example 12 | Example 13 | Example 14 | Example 15 | Example 16 | Example 17 | Example 18 |
|---|---|---|---|---|---|---|---|---|---|
| Catalyst | Cobalt compound<br>(g) | Cobalt<br>acetate<br>1.7800<br>(0.200) | Cobalt<br>acetate<br>0.1330<br>(0.015) | Cobalt<br>acetate<br>1.7800<br>(0.200) | Cobalt<br>acetate<br>1.7800<br>(0.200) | Cobalt<br>acetate<br>0.1330<br>(0.015) | Cobalt<br>acetate<br>0.5330<br>(0.060) | Cobalt<br>acetate<br>0.5330<br>(0.060) | Cobalt<br>acetate<br>0.5330<br>(0.060) |
|  | Manganese compound<br>(g) | Manganese<br>acetate<br>0.1870<br>(0.020) | Manganese<br>acetate<br>0.1410<br>(0.0150) | Manganese<br>acetate<br>0.1870<br>(0.020) | Manganese<br>acetate<br>0.0937<br>(0.010) | Manganese<br>acetate<br>0.1410<br>(0.015) | Manganese<br>acetate<br>0.0468<br>(0.005) | Manganese<br>acetate<br>0.0468<br>(0.005) | Manganese<br>acetate<br>0.0468<br>(0.005) |
|  | Bromine compound<br>(g) | Sodium<br>bromide<br>0.6760<br>(0.250) | Sodium<br>bromide<br>0.3240<br>(0.120) | Sodium<br>bromide<br>0.6760<br>(0.250) | Sodium<br>bromide<br>0.6760<br>(0.250) | Sodium<br>bromide<br>0.3200<br>(0.118) | Sodium<br>bromide<br>0.3240<br>(0.120) | Sodium<br>bromide<br>0.3240<br>(0.120) | Sodium<br>bromide<br>0.3240<br>(0.120) |
|  | Fourth component<br>(g) | Lanthium<br>acetate<br>0.0112<br>(0.002) | Lanthium<br>acetate<br>0.8420<br>(0.158) | Cerium<br>acetate<br>0.0128<br>(0.003) | Cerium<br>acetate<br>0.1260<br>(0.025) | Cerium<br>acetate<br>0.9610<br>(0.191) | Neodynium<br>carbonate<br>0.0585<br>(0.013) | Gadolinium<br>chloride<br>0.0710<br>(0.014) | Holium<br>chloride<br>0.0725<br>(0.015) |
|  | Atomic ratio of<br>fourth component<br>to manganese | 0.04 | 4.2 | 0.05 | 1.0 | 5.0 | 1.0 | 1.0 | 1.0 |
| Properties of<br>terephthallic<br>acid | Appearance<br>Alkaline color<br>4CBA content<br>(p.p.m.)<br>Ashes (p.p.m.) | White<br>0.473<br>970<br><br>5.3 | White<br>0.495<br>590<br><br>3.5 | White<br>0.410<br>913<br><br>4.0 | White<br>0.128<br>212<br><br>2.8 | White<br>0.430<br>553<br><br>2.5 | White<br>0.510<br>623<br><br>4.2 | White<br>0.590<br>817<br><br>4.3 | White<br>0.610<br>790<br><br>4.3 |
| Terephthalic acid yield (%) | | 97.1 | 96.9 | 97.4 | 96.1 | 97.4 | 97.1 | 96.1 | 96.1 |
| Acetic acid recovery<br>ratio (%) | | 92.1 | 91.1 | 92.8 | 92.3 | 92.1 | 89.7 | 88.3 | 89.0 |

Note:
Figure in parentheses means a percentage by weight of metal atoms or bromine atoms in the metal compounds or bromine compound used as the catalyst to acetic acid, respectively.

What is claimed is:

1. A process for producing terephthalic acid, which comprises oxidizing p-tolualdehyde with a gas containing molecular oxygen in a liquid phase using a lower monocarboxylic acid as a solvent and at a temperature in the range of from 120° C. to 260° C. and a pressure in the range of from 0.5 to 50 kg/cm² gauge in the presence of a catalyst consisting of (1) a manganese compound, (2) a cobalt compound, (3) a bromine compound selected from the group consisting of hydrobromic acid, ammonium bromide, sodium bromide, potassium bromide, cesium bromide, magnesium bromide, barium bromide, tetraalkylammonium bromide, tetrabromoethane and tetrabromoparaxylene, and (4) at least one compound selected from the group consisting of chromium compounds, iron compounds, nickel compounds and compounds of metallic elements belonging to the lanthanide series; said at least one compound of component (4) of the catalyst being present in an amount such that the atomic ratio of chromium atoms, iron atoms or nickel atoms to manganese atoms of said manganese compound is from 0.7 to 30.0, or of the metallic element atoms of the lanthanide series to manganese atoms of said manganese compound is from 0.02 to 10.0.

2. A process according to claim 1, wherein the catalyst contains 0.001 to 2.5% by weight of the manganese compound in terms of manganese atoms in the manganese compound, on the basis of the solvent, 0.005 to 0.5% by weight of the cobalt compound in terms of cobalt atoms in the cobalt compound, on the basis of the solvent, 0.05 to 0.5% by weight of the bromine compound in terms of bromine atoms in the bromine compound, on the basis of the solvent, the chromium compound, the iron compound or the nickel compound at an atomic ratio of chromium atoms in the chromium compound, iron atoms in the iron compound, or nickel atoms in the nickel compound to manganese atoms in the manganese compound of 0.7 to 30.0, or the compound of metallic elements belonging to the lanthanide series at an atomic ratio of metallic element atoms in the compound to manganese atoms in the manganese compound of 0.02 to 10.0.

3. A process according to claim 1, wherein the manganese compound is manganese bromide, manganese carbonate, manganese formate, manganese acetate, manganese propionate, manganese butyrate, manganese valerate, or manganese naphthalate.

4. A process according to claim 1, wherein the cobalt compound is cobalt bromide, cobalt carbonate, cobalt formate, cobalt acetate, cobalt propionate, cobalt butyrate, cobalt valerate, or cobalt naphthenate.

5. A process according to claim 1, wherein the chromium compound is chromium bromide, chromium carbonate, chromium oxides, sodium chromate, potassium chromate, chromium formate, chromium acetate, chromium propionate, chromium butyrate, or chromium valerate.

6. A process according to claim 1, wherein the iron compound is iron bromide, iron carbonate, iron oxalate, iron formate, iron acetate, iron propionate, iron butyrate, or iron valerate.

7. A process according to claim 1, wherein the nickel compound is nickel bromide, nickel carbonate, nickel formate, nickel acetate, nickel propionate, nickel butyrate, or nickel valerate.

8. A process according to claim 1, wherein the metal element belonging to the lanthanide series is lanthanum, cerium, praseodymium, neodymium, samarium, europium, gadolinium, terbium, dysprosium, holmium, erbium, thulium, ytterbium, or lutetium.

9. A process according to claim 8, wherein the lanthanum compound is lanthanum chloride, lanthanum bromide, lanthanum carbonate, lanthanum formate, lanthanum acetate, lanthanum propionate, lanthanum butyrate, lanthanum valerate, or lanthanum hydroxide.

10. A process according to claim 8, wherein the cerium compound is cerium chloride, cerium bromide, cerium carbonate, cerium formate, cerium acetate, cerium propionate, cerium butyrate, cerium valerate, or cerium hydroxide.

11. A process according to claim 8, wherein the praseodymium compound is praseodymium chloride, praseodymium bromide, praseodymium carbonate, praseodymium formate, praseodymium acetate, praseodymium propionate, praseodymium butyrate, praseodymium valerate, or praseodymium hydroxide.

12. A process according to claim 8, wherein the neodymium compound is neodymium chloride, neodymium bromide, neodymium carbonate, neodymium formate, neodymium acetate, neodymium propionate, neodymium butyrate, neodymium valerate, or neodymium hydroxide.

13. A process according to claim 8, wherein the samarium compound is samarium chloride, samarium bromide, samarium carbonate, samarium formate, samarium acetate, samarium propionate, samarium butyrate, samarium valerate, or samarium hydroxide.

14. A process according to claim 8, wherein the europium compound is europium chloride, europium bromide, europium carbonate, europium formate, europium acetate, europium propionate, europium butyrate, europium valerate, or europium hydroxide.

15. A process according to claim 8, wherein the gadolinium compound is gadolinium chloride, gadolinium bromide, gadolinium carbonate, gadolinium formate, gadolinium acetate, gadolinium propionate, gadolinium butyrage, gadolinium valerate, or gadolinium hydroxide.

16. A process according to claim 8, wherein the terbium compound is terbium chloride, terbium bromide, terbium carbonate, terbium formate, terbium acetate, terbium propionate, terbium butyrate, terbium valerate, or terbium hydroxide.

17. A process according to claim 8, wherein the dysprosium compound is dysprosium chloride, disprosium bromide, dysprosium carbonate, dysprosium formate, dysprosium acetate, dysprosium propionate, dysprosium butyrate, dysprosium valerate, or dysprosium hydroxide.

18. A process according to claim 8, wherein the holmium compound is holmium chloride, holmium bromide, holmium carbonate, holmium formate, holmium acetate, holmium propionate, holmium butyrate, holmium valerate, or holmium hydroxide.

19. A process according to claim 8, wherein the erbium compound is erbium chloride, erbium bromide, erbium carbonate, erbium formate, erbium acetate, erbium propionate, erbium butyrate, erbium valerate, or erbium hydroxide.

20. A process according to claim 8, wherein the thulium compound is thulium chloride, thulium bromide, thulium carbonate, thulium formate, thulium acetate, thulium propionate, thulium butyrate, thulium valerate, or thulium hydroxide.

21. A process according to claim 8, wherein the ytterbium compound is ytterbium chloride, ytterbium bromide, ytterbium carbonate, ytterbium formate, ytterbium acetate, ytterbium propionate, ytterbium butyrate, ytterbium valerate, or ytterbium hydroxide.

22. A process according to claim 8, wherein the lutetium compound is lutetium chloride, lutetium bromide, lutetium carbonate, lutetium formate, lutetium acetate, lutetium propionate, lutetium butyrate, lutetium valerate, or lutetium hydroxide.

23. A process according to claim 1, wherein the lower aliphatic monocarboxylic acid is acetic acid, propionic acid or butyric acid.

24. A process according to claim 23, wherein the solvent is an amount of at least twice by weight as much as the weight of p-tolualdehyde.

25. A process according to claim 1, wherein the gas containing molecular oxygen is air.

* * * * *